(12) United States Patent
Bastide et al.

(10) Patent No.: US 10,617,362 B2
(45) Date of Patent: Apr. 14, 2020

(54) MACHINE LEARNED OPTIMIZING OF HEALTH ACTIVITY FOR PARTICIPANTS DURING MEETING TIMES

(71) Applicant: International Business Machines Corporation, Armonk, NY (US)

(72) Inventors: Paul R. Bastide, Boxford, MA (US); Filiz Isabell Kiral-Kornek, Collingwood (AU); Dwarikanath Mahapatra, Melbourne (AU); Susmita Saha, Coburg (AU); Arun Vishwanath, Blackburn (AU); Stefan von Cavallar, Sandringham (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/341,597

(22) Filed: Nov. 2, 2016

(65) Prior Publication Data

US 2018/0116599 A1    May 3, 2018

(51) Int. Cl.
*A61B 5/00* (2006.01)
*H04M 3/56* (2006.01)
(Continued)

(52) U.S. Cl.
CPC .......... *A61B 5/7267* (2013.01); *A61B 5/0022* (2013.01); *A61B 5/1112* (2013.01);
(Continued)

(58) Field of Classification Search
CPC ..... A61B 5/021; A61B 5/0002; A61B 5/1118; G06F 19/3481; A63B 24/0062
See application file for complete search history.

(56) References Cited

U.S. PATENT DOCUMENTS

| 3,964,196 A | 6/1976 | Ureta |
| 5,959,662 A | 9/1999 | Shaffer et al. |

(Continued)

FOREIGN PATENT DOCUMENTS

| CN | 202736243 U | 2/2013 |
| CN | 103500397 A | 1/2014 |

(Continued)

OTHER PUBLICATIONS

Likamwa, R., et al.,"MoodScope: Building a Mood Sensor from Smartphone Usage Patterns", http://www.ruf.rice.edu/~mobile/publications/likamwa2013mobisys2.pdf, MobiSys '13, Jun. 25-28, 2013, Accessed on Oct. 31, 2016, 13 pages.

(Continued)

*Primary Examiner* — Patrick Fernandes
(74) *Attorney, Agent, or Firm* — Scully, Scott, Murphy & Presser, P.C.; Joseph Petrokaitis

(57) ABSTRACT

Providing an activity for a participant may include receiving at least location data specifying a location of the participant. An engagement level of the participant may be predicted based on the location data. Sensor data associated with the participant may be received, the sensor data comprising at least current physiological data associated with the participant. Based at least on the predicted engagement level and the sensor data, an exercise for the participant to perform may be determined. A notification signal may be transmitted to the participant to perform the exercise.

15 Claims, 5 Drawing Sheets

(51) Int. Cl.
*H04W 4/02* (2018.01)
*A61B 5/11* (2006.01)
*G16H 20/00* (2018.01)
*G16H 20/30* (2018.01)

(52) U.S. Cl.
CPC .......... *A61B 5/1118* (2013.01); *A61B 5/6898* (2013.01); *G16H 20/30* (2018.01); *H04M 3/56* (2013.01); *H04W 4/027* (2013.01); *A61B 5/486* (2013.01); *A61B 2503/10* (2013.01); *A61B 2503/12* (2013.01); *A61B 2562/0219* (2013.01); *H04M 2242/15* (2013.01); *H04M 2250/10* (2013.01); *H04M 2250/12* (2013.01)

(56) References Cited

U.S. PATENT DOCUMENTS

| | | | |
|---|---|---|---|
| 6,679,817 | B1 | 1/2004 | Williams |
| 6,985,078 | B2 | 6/2006 | Suzuki et al. |
| 7,095,328 | B1 | 8/2006 | Stern et al. |
| 2002/0083122 | A1 | 6/2002 | Lemchen |
| 2005/0102172 | A1 | 5/2005 | Sirmans, Jr. |
| 2006/0111944 | A1 | 5/2006 | Sirmans, Jr. et al. |
| 2006/0230108 | A1 | 10/2006 | Tatsuta et al. |
| 2008/0040187 | A1* | 2/2008 | Carraher ............. G06Q 10/109 705/7.19 |
| 2008/0167056 | A1 | 7/2008 | Gilzean et al. |
| 2009/0009320 | A1 | 1/2009 | O'Connor et al. |
| 2012/0020649 | A1* | 1/2012 | Vanderkaden ....... G11B 27/034 386/280 |
| 2015/0238817 | A1* | 8/2015 | Watterson .......... A63B 24/0087 482/8 |
| 2016/0232131 | A1* | 8/2016 | Liu ....................... G06F 17/211 |
| 2017/0065851 | A1* | 3/2017 | Deluca ............... A63B 24/0087 |

FOREIGN PATENT DOCUMENTS

| | | |
|---|---|---|
| CN | 104257145 A | 1/2015 |
| EP | 2264988 A1 | 12/2010 |

OTHER PUBLICATIONS

Ramnath, J., "Find time for your goals with Google Calendar", https://blog.google/products/calendar/find-time-goals-google-calendar/, Google, Apr. 12, 2016, Accessed on Oct. 31, 2016, 8 pages.

Shellenbarger, S., "Surviving a Conference Call How to Stop the Rambling, Multitasking and Zoning Out", http://www.wsj.com/articles/SB10001424052702304610404579405221066665830, The Wall Street Journal, Updated Feb. 26, 2014, Accessed on Nov. 1, 2016, 4 pages.

Steur, T., "How to track Mobile apps usage (clicks, phones, errors, etc.) or track software analytics", http://piwik.org/blog/2012/04/how-to-use-piwik-to-track-mobile-apps-activity-clicks-phones-errors-etd, PIWIK, Apr. 9, 2012, Accessed on Oct. 31, 2016, 13 pages.

* cited by examiner

MACHINE LEARNED OPTIMIZING OF HEALTH ACTIVITY FOR PARTICIPANTS DURING MEETING TIMES

FIELD

The present application relates generally to computers and computer applications, and more particularly to monitoring user activity via sensor devices and providing health activity for a participant in a meeting.

BACKGROUND

There are many scenarios in which a user is attending a meeting such as a conference call or a talk in which the user is not an active participant, but acts as more of a passive listener. Conference calls and presentations (or talks) are a way of life for people working in offices, businesses, universities, and other similar settings. It is recognized that most conferencing is done by audio calls, and the amount of time spent on audio conference calls is expected to grow. In this context, there is an opportunity to efficiently fit a physical activity during these times for the purpose of attaining pre-defined fitness and health goals.

BRIEF SUMMARY

A system and method of providing heath activity for a participant in a conference call may be provided. The system, in one aspect, may include a predictive system executing on at least one hardware processor, the predictive system operable to train a machine model based on parameters labeled by analyzing historical pattern of engagement. The parameters may include a type of a conference meeting, a number of conference meetings being conducted at a time, agenda participation, location, context of the conference meeting, and a type of equipment used in the conference meeting. The predictive system may receive data associated with the conference call and location data specifying a location of the participant conducting the conference call. The predictive system may predict an engagement level of the participant that is to participate in the conference call based on the received data and the location data by executing the trained machine model with the received data and the location data as input to the trained machine model. A reactive system executing on at least one hardware processor may be coupled to at least one sensor device, and detect sensor data including at least current physiological data associated with the participant via the at least one sensor device. A decision making system executing on at least one hardware processor may identify the participant's fitness goal stored in a network. Based on the predicted engagement level, the sensor data and the participant's fitness goal, the decision making system may determine an exercise for the participant to perform during the conference call. The decision making system may transmit a notification signal to the participant to perform the exercise.

A method of providing heath activity for a participant in a conference call, in one aspect, may include receiving data associated with the conference call and location data specifying a location of the participant conducting the conference call. The method may also include predicting an engagement level of the participant that is to participate in the conference call based on the received data and the location data by executing a trained machine model with the received data and the location data as input to the trained machine model. The method may further include receiving sensor data associated with the participant, the sensor data comprising at least current physiological data associated with the participant. The method may also include identifying the participant's fitness goal stored in a network. The method may further include, based on the predicted engagement level, the sensor data and the participant's fitness goal, determining an exercise for the participant to perform during the conference call. The method may also include transmitting a notification signal to the participant to perform the exercise.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

DETAILED DESCRIPTION

Figure 1:
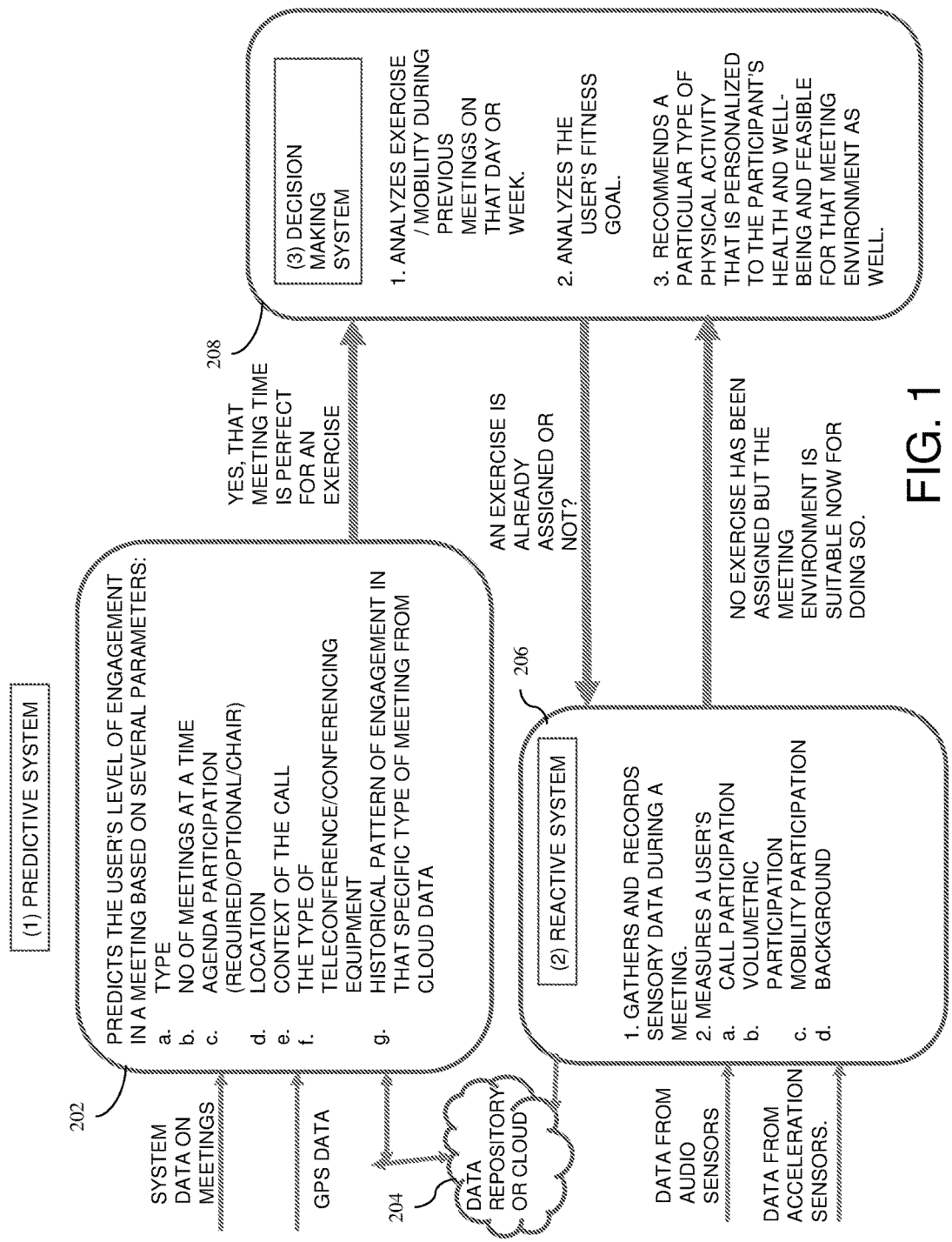
FIG. 1 is another block diagram illustrating system components in one embodiment of the present disclosure.
Figure 2:
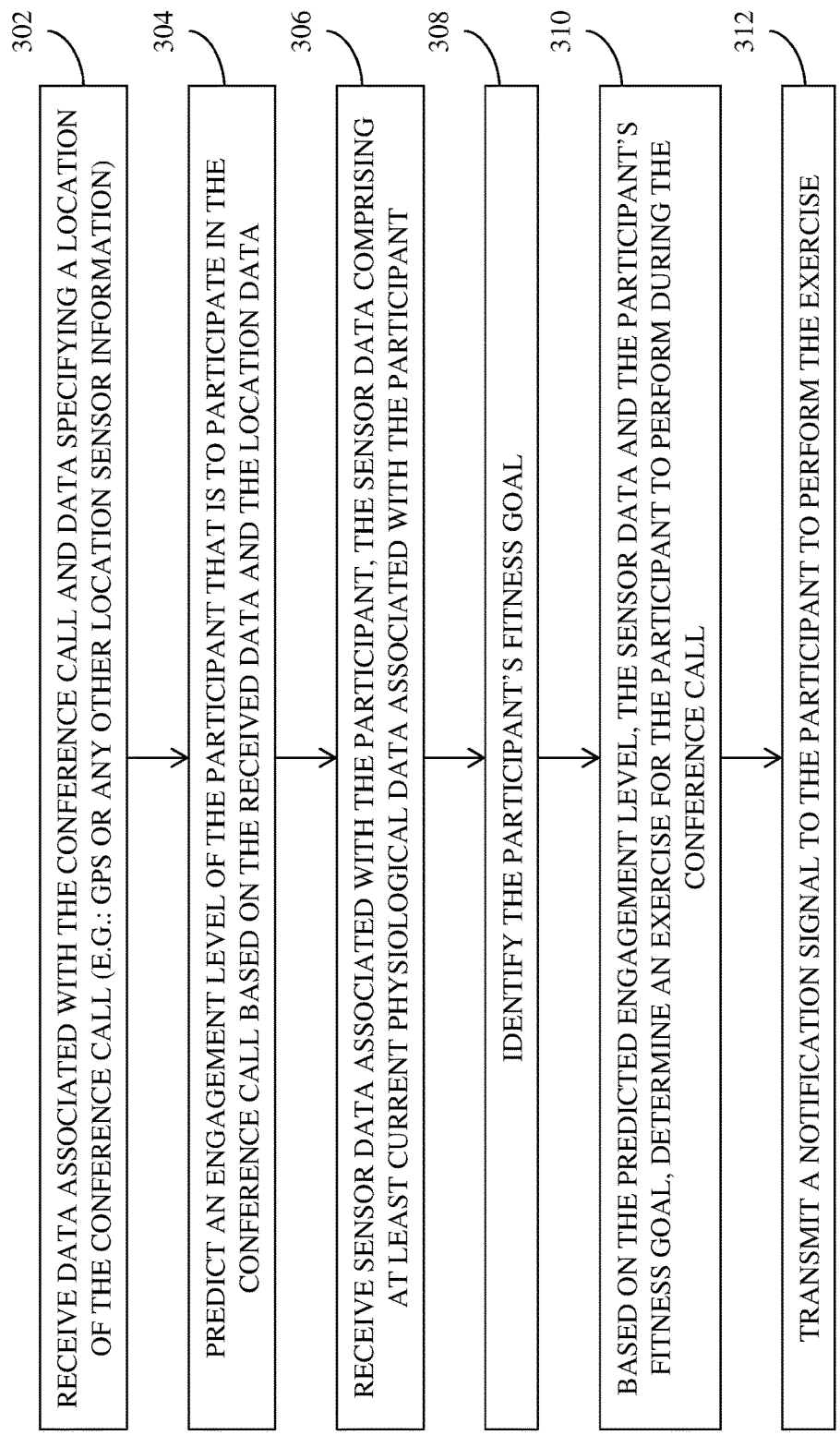
FIG. 2 is a flow diagram illustrating a method in one embodiment of the present disclosure.

A system and method in one embodiment may monitor a participant's activity pattern during a passive listening time while in a conference call or the like meeting, and accordingly recommend a particular type of physical activity to improve the participant's physical and mental fitness levels. The system and method, in one aspect, may detect a participant's activity pattern and produce a signal that recommends a physical activity, for example, to suggest instant and appropriate exercise routines at the user's idle times during a meeting. In one embodiment, the suggested activity is directly correlated with a personalized health and fitness goals for the user.

The system and method in one embodiment works to detect the low-engagement meeting times for a user through a combination of predictive and reactive algorithm, and accordingly recommends suitable physical activity during those times. The predictive system suggests exercises based on the system information available before the meeting or at the onset of the meeting (e.g., location identification). The reactive system gathers real time data during a meeting which serves the following purposes: Contributes in building historical data pattern and assists the predictive system; In case, the predictive system decides a meeting to be not appropriate for exercises, the reactive system is still able to independently identify if the overall meeting environment (e.g., location or another environment) and engagement (whether the user commenting at all) are now suitable for an exercise and vice versa.

Leveraging the user's wearable fitness device and smartphone, the system and method may automatically determine and recommend activities to engage in for improving the user's health and wellbeing during the passive time spent by the user during a conference call or a like meeting. For instance, the smartphone may be installed with an app or application that provides detailed statistics of the user's mobile phone usage (e.g., applications, web browsing, screen activation, and/or others). A user's wearable fitness device may be interfaced with the smartphone, and together they detect in real-time the user's participation in the conference call. This may be achieved explicitly by detecting whether the user is moving or not during the meeting, and/or implicitly via the app in the smartphone that analyzes the phone's usage pattern (e.g., how often the user is engaged in the meeting using the phone's audio sensors). By analyzing the historical data of the user's activity in various conference calls, a profile can be created for the user in terms of how engaging the user is during the meetings.

The app then recommends to the user an appropriate set of mental and physical exercises that is based on the idleness index measured by the smartphone app and the sensory data from the fitness device such as the blood pressure and heart rate measurement device, and the set goal for fitness.

The system and method, for example, may be designed for usage in a meeting environment, for instance, to effectively estimate and use the idle state of a person during work times, to achieve the person's own fitness goal. The system and method, for example, include predicting the participant's involvement during the meeting times; analyzing the goal set by the participant, for example, in terms of how many calories to burn during a day; suggesting instant exercise routines that are personalized to the participant's health and well-being (e.g., sit, stand, squat exercise at least 15 times in 10 minutes can burn 50 calories).

The system and method in one embodiment provides the advantages of being able to exploit the time available during meetings or talks for improving health and well-being, improve lifestyle, and improve technology associated with wearable devices.

Components implementing a system in one embodiment of the present disclosure are executable on one or more hardware processors. In one embodiment, the system may predict a participant's involvement in a conference call by an app (application) installed in a smartphone or the like device. Predicting the user level of engagement during a conference call can be achieved in a number of different ways, for example, by the smartphone application or the like. For instance, the app running or executing in the phone or the like device may monitor audio sensors coupled to the smartphone, the time of the call, the location of the user (e.g., at home, at work, or another location), who initiated the call, how many participants are there in the call. Other information may be monitored by the app or the like. As another example, during the meeting the app may record the duration of user engagement, when the user tends to be active (e.g., during the start of the call), whether the user is repeatedly using his phone to check for new messages or emails, reading news or sports updates, or using it in different ways to keep himself occupied. This enables the app or the like to build a profile of user engagement. The built profile of the user engagement may be used, e.g., in conjunction with a wearable device, to predict the involvement of a user during a conference call.

In one embodiment, current health condition of the user may be predicted using a wearable fitness device. For instance, the wearable device is able to detect if the participant is sedentary or not for a particular duration (e.g., during a conference call) by monitoring the user's physiological parameters (such as heart rate, blood pressure, and/or others), user's special inputs (hunger or headaches) and recording any physical activity made by the user for that particular day (e.g., taking steps, and/or another activity). The fitness device communicates these parameters to the app or the like in the smartphone.

A decision making app (application or the like) may suggest an appropriate health activity, based on the input from the smartphone app and the wearable device. For instance, a decision making app receives all the parameters from the above two subsystems. The decision making app may be also connected with a data cloud, which may serve the information about user's general health data, e.g., height, weight, medical condition, and his personalized fitness goal. The decision making app is able to recommend a particular and feasible type of physical or mental activity to improve the user's fitness and concentration levels (e.g., shoulder exercises for 10 minutes), which may help to achieve his fitness goal more efficiently.

The system in one embodiment of the present disclosure works to detect the low-engagement meeting times for a user through a combination of predictive and reactive algorithm, and accordingly recommends suitable physical activity during those times. The predictive system in one embodiment suggests exercises based on the system information available before the meeting, or for example, at the onset of the meeting (e.g., based on location identification). The reactive system in one embodiment gathers real time data during a meeting, which serves the following purposes: Contributes in building historical data pattern and assists the predictive system; In case the predictive system decides a meeting to be not appropriate for exercises, the reactive system is still able to independently identify if the overall meeting environment (e.g., location) and engagement level (e.g., is the user commenting at all or actively participating?) are now suitable for an exercise and vice versa.

FIG. 1 is a block diagram illustrating system components in one embodiment of the present disclosure. The components may run or execute on one or more hardware processors. A predictive system 202 predicts the user's level of engagement in a meeting based on parameters. Examples of the parameters include type, number of meetings at a time and mode of the meetings, agenda participation, location, context of the call, the type of teleconference or conferencing equipment, and historical pattern of engagement in that specific type of meeting. The data or part of the data associated with the parameters may be obtained from one or more of system data on meetings, global positioning system data, and the cloud or another data repository 204.

The type parameter specifies or describes the type of the call, for example, talk, general or audio conferencing call. Examples of the types of the call may include seminar presentations, in-house meeting where participants are all present in person, and meetings conducted via audio conferencing.

The number of meetings at a time and mode of the meetings parameters specify how many meetings are being conducted at a time and the mode of the meetings. For instance, while many users may schedule one meeting at a time, others may have more than one meeting at a time. The mode of the meeting or meetings may describe or specify the user's input to the system about the user's probable mode to chat when the user accepted or initiated the meeting request, for example, listening mode or talking mode.

Agenda participation parameter may specify or describe the participation role of the user in the meeting and/or participation information. Examples of this parameter may include information such as, is the user the chair of the meeting? Is the user listed as a speaker? Is the user listed as a FYI ("for your information") only? Is the meeting required or optional for the user? The number of participants.

The location parameter specifies the geographic location of the user during the meeting. As an example, if the user provides an input in the system that during a particular audio conferencing call the user will be connected from home, the system may be more prone to suggest exercises such as walking around or walking on a treadmill in home environment while listening to the conference call, which may be suitable. In an office environment, walking may distract others.

As another example, the user may input that the user is in a location such as a train, and cannot participate as an active speaker in the meeting, for instance, due to background noise. The user may also input that when the user gets to the train station, where the user has joined many calls, the user normally sits down in a corner.

A system in one embodiment of the present disclosure may suggest that if the user has taken less number of steps for the day, that the user gets up and walks around to get more steps while participating in the call. Such location and location related information may be utilized to predict user's level of engagement in a meeting.

The context of the call parameter specifies the context of the user in the call or conference such as the likelihood of the user's participation. For example, user A is an engineer on product A; User A is part of an organization that is building A and B; User A is invited to a meeting to discuss the status, User A is there to back up the user's manager during the update on A. User A's manager is scheduled to go second on the agenda. The predictive system 202, for example, may calculate that User A is a required participant and unlikely to speak on all topics in the meeting based on this example context. For example, the predictive system 202 may calculate a 50% likelihood that User A is to speak. An example notification pushed to user A may include a recommendation that user A walk around a building while dialed into the call. In one aspect, weather, construction, traffic conditions and/ or routing patterns, may be considered, for example, if suggesting a specific route.

The type of teleconference/conferencing equipment parameter may specify information about the equipment such as whether it is a listen only communication line or a two way line, whether it is half or full duplex lines, whether it require software on the computer to attend the conference call or meeting. In one aspect, the listen only line versus duplex/half duplex indicates the ability to participate, for example, indicating the likelihood of participation. For instance, equipment with half duplex capability, if user B is speaking, user A may only be received by user B when user B is done talking.

Historical pattern of engagement in that specific type of meeting parameter provides historical information. For instance, the system of the present disclosure is able to store both the predictive-system and real-time data from previous meetings in a data cloud 204 or the like, and is able to indicate the likelihood of meeting participation for the present meeting. This type of historical data may be used to assist the predictive system to decide about exercises. In addition, such data may help a user to identify areas where a user may need additional training or exercise to increase the user's likelihood of participation. For instance, exercising may cause a person to be more alert, and increase the likelihood the user will participate, e.g., in this or next meeting. As another example, the system may suggest calisthenics which isolate the person in place/near the phone based on the likelihood of movement pattern obtained from the historical data.

As an example, a decision tree based supervised learning method may be implemented to predict the level of user's engagement in a meeting. In one embodiment, the level of user's engagement in a meeting may be determined in terms of high, low, or medium. In another embodiment, the level of user's engagement in a meeting may be determined as an average percentage of engaged times during meetings. The historical data enables annotating a user's level of engagement in the present context by taking into account the real-time parameters described above. For example, parameters 202 $a$-$f$ may be fed into a machine learning algorithm, labeled with the previous engagement level in the historical pattern data 202 $g$. Given historical data, the algorithm builds a model that is able to predict the engagement level of a meeting participant. Any new data (206 $a$-$d$) provides additional training data for the machine-learning algorithm. The built model is executed to predict an engagement level for the current call. For instance, the built model takes as input current context of the call, for example, including the type, number of meetings at a time, location, context of the call, the type of teleconference, sensory data, call participation, volumetric participation, mobility participation and background, and predicts the engagement level. Based on the predicted engagement level and real-time environment variables (206 $a$-$d$), exercises are chosen for recommendation.

A reactive system 206 continuously gathers different sensory data, analyzes the data, stores parameter values in data cloud 204 or another repository, and may initiate an exercise request if necessary and suitable. The data may be gathered from audio sensor(s) and acceleration sensor(s). The reactive system 206 gathers the data in real-time, for example, while the conference or call is being conducted. The parameter values the reactive system stores may include call participation, volumetric participation, mobility participation, and background data.

Call participation parameter may describe participation level of a user. For example, call participation parameter may specify whether the user is talkative on the call and/or topic of the call, whether the user is engaged in discussions on the topic, whether the user is involved in another call at the same time, for example, whether the user has more than one number active at a time, whether the user is dialed in to multiple calls.

Volumetric participation parameter may describe the amount or volume of participation by the user. For example, this parameter may specify whether the user is normally talkative on this type of call, whether the user is reserved, whether the user has any comments, distance from two standard deviations of engagement for this user. This data can be measured using a microphone, such as the participant's cell phone. The data may be quantified as a percentage of engagement over time, and stored in the data-cloud, connected to the user's profile.

Mobility participation parameter may describe the level or amount of user's motion. For example, this parameter may specify whether the user is moving, whether the user is in a vehicle such as a car, the global positioning system (GPS) situation for the user, whether the GPS coordinates are continually moving, the extent of the user's physical activity during a meeting, whether the user is moving too much or not at all. This data can be measured using a GPS sensor, for example of the participant's cell phone. The data may be quantified as a measured amount movement over time, and stored in the data-cloud, connected to the user's profile.

Background parameter describes the meeting environment. For example, this parameter may specify whether the user is in a conference room with multiple people, for example, can other voices be heard from other participants, whether there are intermittent noises. This data can be measured using a microphone, such as the participant's cell phone. Using filtering, sounds by sources other than the user may be quantified as a percentage of noise over time, and stored in the data-cloud, connected to the user's profile.

A decision making system 208 receives the meeting participation indicator values (e.g., parameter values described above) from the predictive system 202 and reactive system 206. The decision making system analyzes the daily and/or weekly fitness goal set for the participant, for example, in terms of how many calories to burn during a day or what types of exercises one should do regularly. This type of information may be gathered from a data cloud or other information sources, for example, social network server, direct user input, and/or others.

Based on the participation indicator values and the user's fitness goal, the decision making system 208 recommends a particular type of physical activity that is personalized to the participant's health and well-being and feasible for that meeting environment as well. For instance, a sit stand squat exercise may be suggested for a conference call. As another example, a simple shoulder exercises in a seminar talk may be recommended. Yet another example may include an exercise using a lightweight, silent in operation exercise device.

The predictive system module 202 makes the decision as to whether the meeting time is suitable for doing an exercise or not via a set machine learning algorithms and sends a yes or no signal to the decision making system module 208. At 208, all necessary variables (predicted user participation level determined at 202 and environment variables determined at 206) are stored in a look-up table with suitable exercises (for example: high participation likelihood, bad weather→shoulder exercise; low participation likelihood, good weather, low noise in the environment→go for a walk). Whether the weather is good or bad may be determined based on a number of criteria meeting a threshold requirement for determining whether the weather is good or bad. In one embodiment, this look-up table is stored globally. A modified version that takes user input into account (e.g., "this exercise doesn't work for me") may be stored in the data-cloud, connected to a user's profile. The module 208 sends feedback to the reactive system module 206 about the status of assignment of any physical activity (YES/NO). The reactive system module 206 continually monitors the real-time activities of a user during the meeting time. If it finds that the meeting time is now suitable for an activity assignment, for example, via the predictive system based on the current activity status of the user, it sends back the yes signal to 208. The decision making system 208 re-evaluates the decision and consults the look-up table to assign an exercise.

In this way, the system of the present disclosure in one embodiment is able to use these predicted low engagement meeting times to meet the user's daily fitness goal time efficiently and to improve on a possible sedentary lifestyle.

Figure 3:
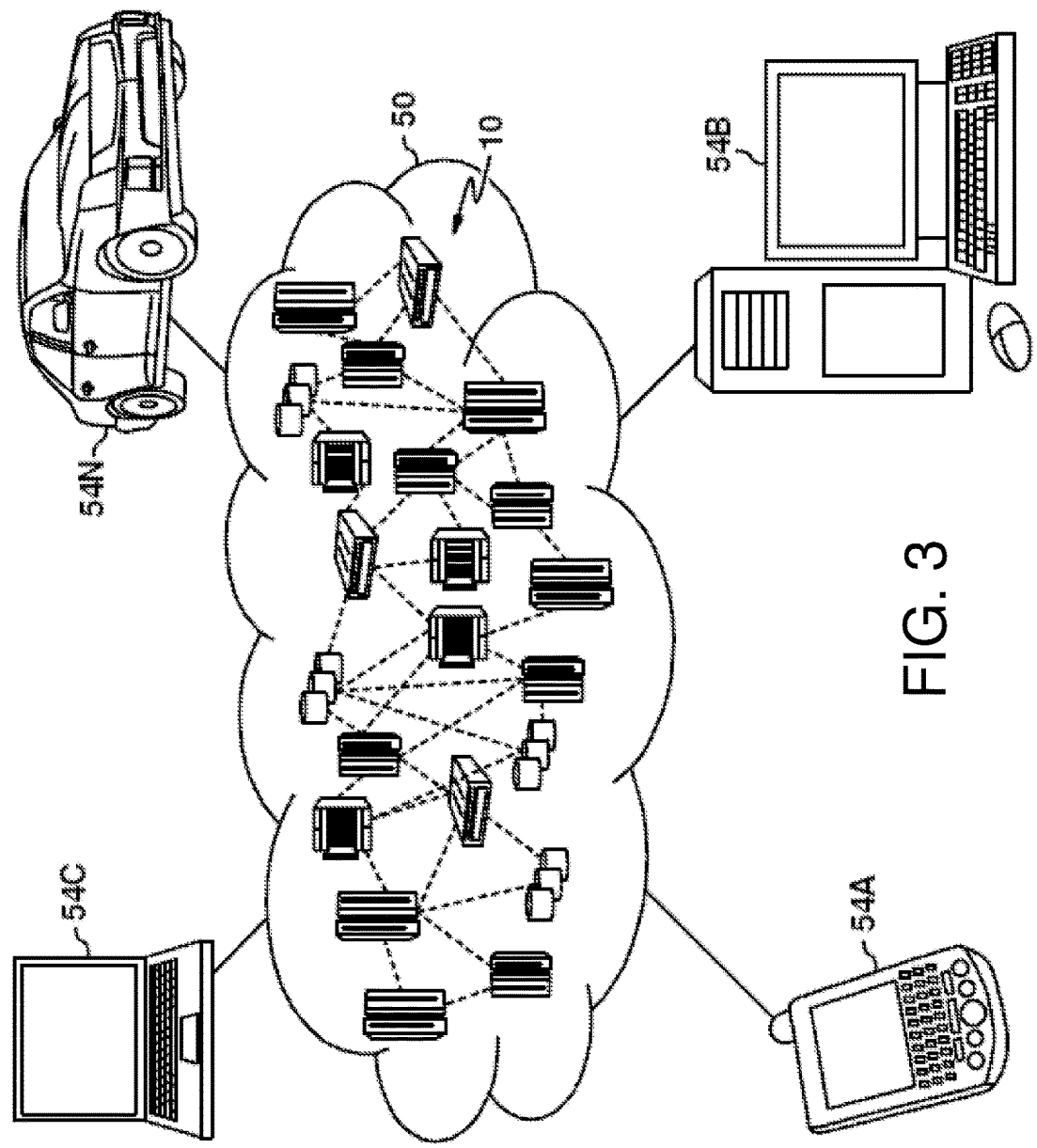
FIG. 3 illustrates cloud computing environment in one embodiment of the present disclosure.

FIG. 3 is a flow diagram illustrating a method in one embodiment of the present disclosure. The method, for example, monitors a participant's physical activity level, for example, via a wearable sensor and/or smartphone and identifies health activity that can be performed during a conference call or the like.

At 302, data associated with the conference call and data specifying a location of the conference call are received, location of the user conducting the conference call. The data specifying a location of the conference call may be GPS data and/or any other location sensor information.

At 304, an engagement level of the participant that is to participate in the conference call is predicted based on the received data and the location data. In one embodiment, a decision tree based supervised learning method may be implemented to predict the level of user's engagement in a meeting. In one embodiment, the level of user's engagement in a meeting may be determined in terms of high, low, or medium. In another embodiment, the level of user's engagement in a meeting may be determined as an average percentage of engaged times during meetings. Historical data enables automatically annotating a user's level of engagement in the present context by taking into account the real-time parameters associated with the user. Example of a real-time parameter includes measured background or loudness level. Using the audio recording obtained through a microphone, for example from the user's mobile phone, any time the loudness level exceeds a defined threshold level, the time is labeled as a time the user speaks. The annotated data is used as an input to the decision tree to train the decision tree to suggest appropriate exercise/health activities in alignment with the user's fitness goal. The trained decision tree is executed to predict the engagement level based on the current parameters.

At 306, sensor data associated with the participant is received. The sensor data may include at least current physiological condition associated with the participant, for example, heart rate, blood pressure and/or others. The sensor data may be received from a sensor device coupled to a smartphone, for example. An app installed on the smartphone may process the sensor detected data.

At 308, the participant's fitness goal may be identified. For example, such goal may be identified based on data stored on a data cloud. For instance, a personalized fitness goal based on the user's health parameters and medical data may be stored in the data cloud, and accessed for determining exercises, if any, to perform during a meeting.

At 310, based on the predicted engagement level, the sensor data and the participant's fitness goal, an exercise for the participant to perform during the conference call may be determined. For instance, one or more exercises may be suggested by performing a look up of previously suggested routines for the user given the parameter settings.

At 312, a notification signal is transmitted to the participant recommending the participant perform the determined exercise.

The following scenario describes an example use case in one embodiment. Consider the following parameters as the current or real-time call information or context. The current date/time is Thu 3 pm. A computer processor may automatically access a user's calendar information to learn the following parameters: 1. The user will participate in a meeting starting at 3.30 pm and that the meeting will last for 60 minutes; 2. The 'TYPE' of the meeting is 'TEAM MEETING'; 3. The 'NO OF MEETINGS AT A TIME' is 1; 4. The user is stated as an optional for the 'AGENDA PARTICIPATION'; 5. The location of the user is 'OFFICE'; 6. The 'CONTEXT OF THE CALL' is 'Backup user's manager'; 7. The 'TYPE OF TELECONFERENCING' is 'Audio Conference'. Given these attributes, the predictive system (FIG. 1 at 202) runs a set machine learning algorithm to predict that the likelihood of user engagement in the meeting is low, for example, 15%. Given this likelihood estimate, the predictive system (FIG. 1 at 202) sends a 'YES' signal to the decision making system (FIG. 1 at 208) indicating that the period between 3:30 pm and 4:30 pm is an appropriate time for doing an exercise. Taking into account the local weather forecast, for example, automatically determined from connecting to a weather system or the like, the decision making system (FIG. 1 at 208) determines that it will be sunny for the duration of the meeting. The decision making system (FIG. 1 at 208) notes that earlier in the day, the user has been mobile (e.g., by accessing and analyzing the GPS traces stored in the mobile device), and the user has set a fitness goal of achieving 15,000 steps for the day, but has achieved only 7,000 steps so far. For example, the number of steps can be tracked from a health/fitness device worn by the user. The decision making system (FIG. 1 at 208) therefore recommends that the user 'GOES FOR A WALK OUTSIDE'. Given that the weather is sunny, the decision making system (FIG. 1 at 208) also may suggest a route for the walk, which the decision making system (FIG. 1 at 208) knows will take about 60 minutes to complete (based on accessing and analyzing the user's stride length and previously traversed information), and will account for about 6000 steps.

Embodiments of the present invention are capable of being implemented in conjunction with any other type of computing environment now known or later developed, for example, including a cloud computing environment. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
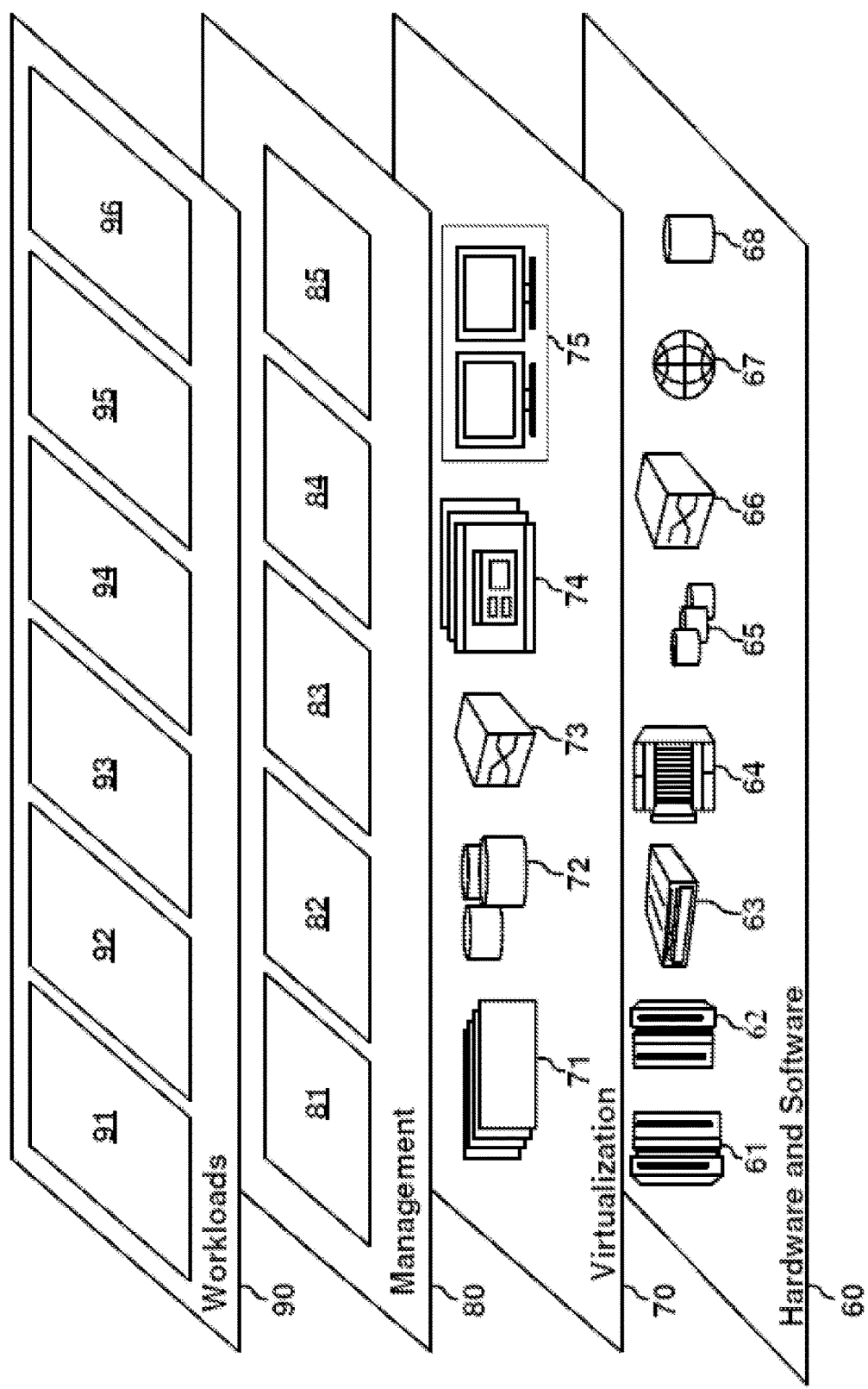
FIG. 4 illustrates a set of functional abstraction layers provided by cloud computing environment in one embodiment of the present disclosure.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
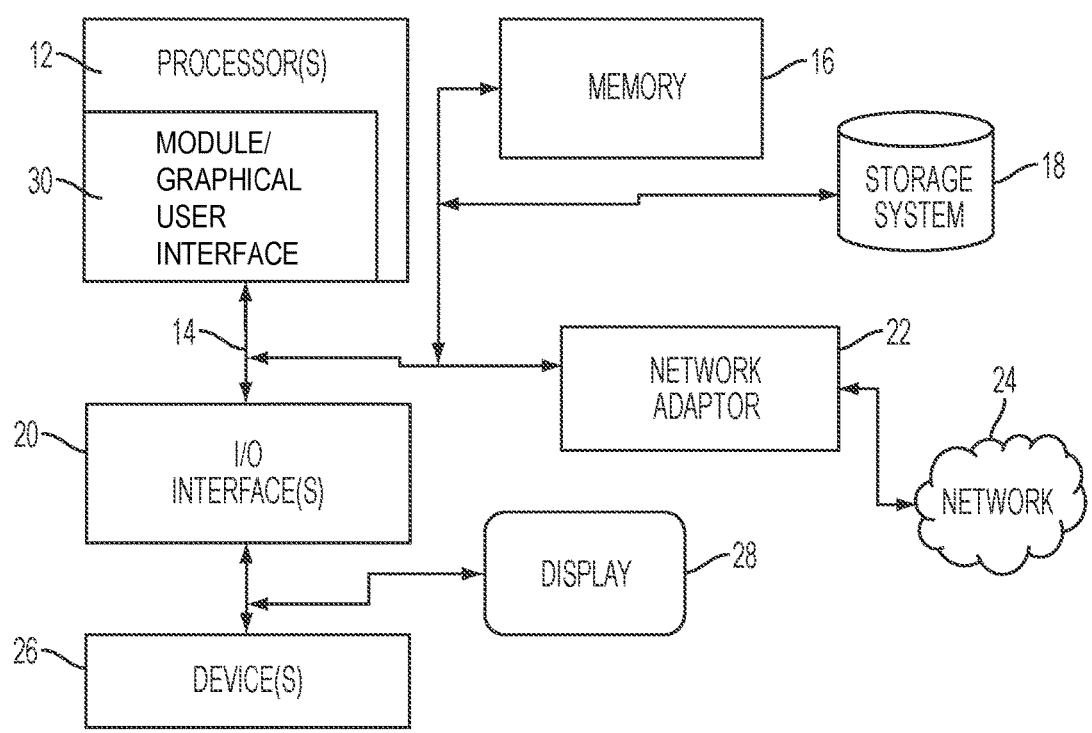
FIG. 5 illustrates a schematic of an example computer or processing system that may implement a health activity recommendation system described above, in one embodiment of the present disclosure.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and another processing 96, for example, a decision making system, and/or data cloud.

FIG. 6 illustrates a schematic of an example computer or processing system that may implement a health activity recommendation system described above, in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A method of providing health activity for a participant in a conference call, the method performed by a hardware processor, comprising:
receiving data associated with the conference call and location data specifying a location of the participant conducting the conference call; predicting an engagement level of the participant that is to participate in the conference call based on the received data and the location data by executing a trained machine model with the received data and the location data as input to the trained machine model, the trained machine model trained based on labeled historical data comprising at least historical data associated with historical conference calls and associated historical location data and historical engagement levels, the trained machine model trained to predict a level of engagement of the participant indicating how actively the participant participates in a meeting;
receiving sensor data associated with the participant, the sensor data comprising at least current physiological data associated with the participant;
identifying the participant's fitness goal stored in a network;
based on the predicted engagement level, the sensor data and the participant's fitness goal, determining an exercise for the participant to perform during the conference call from a predefined lookup table of suggested exercises,
wherein the hardware processor is a component of a smartphone device, the smartphone device interfaced with a plurality of wearable devices worn by the participant, the plurality of wearable devices continuing to communicate real-time physiological sensor data to the smartphone device during the conference call,
wherein the hardware processor further monitors during the conference call, an audio sensor coupled to the smartphone to determine current engagement level of the participant during the conference call,
wherein the determining an exercise for the participant to perform during the conference call comprises at least:
automatically updating a decision determined based on the predicted engagement level that an exercise should not be recommended, to recommending the exercise based on the real-time physiological sensor data and the current engagement level of the participant during the conference call, and
transmitting a notification signal to the participant during the conference call.

2. The method of claim 1, wherein the data comprises a type of the conference meeting, a number of conference meetings being conducted at a time, agenda participation, context of the conference meeting, and a type of equipment used in the conference meeting.

3. The method of claim 1, wherein the labeled historical data comprise a type of a conference meeting, a number of conference meetings being conducted at a time, agenda participation, location, context of the conference meeting, and a type of equipment used in the conference meeting.

4. The method of claim 3, wherein the machine model is further trained based on sensor parameter data.

5. The method of claim 1, wherein the sensor data further comprises acceleration data from an acceleration sensor coupled to the smartphone device that measures acceleration.

6. The method of claim 1, wherein the machine model comprises a decision tree trained based on supervised machine learning algorithm.

7. A non-transitory computer readable storage medium storing a program of instructions executable by a machine to perform a method of providing heath activity for a participant in a conference call, the method comprising:
receiving data associated with the conference call and location data specifying a location of the participant conducting the conference call;
predicting an engagement level of the participant that is to participate in the conference call based on the received data and the location data by executing a trained machine model with the received data and the location data as input to the trained machine model, wherein the trained machine model is trained based on labeled historical data comprising at least historical data associated with historical conference calls and associated historical location data and historical engagement levels, the trained machine model trained to predict a level of engagement of the participant indicating how actively the participant participates in a meeting;
receiving sensor data associated with the participant, the sensor data comprising at least current physiological data associated with the participant;
identifying the participant's fitness goal stored in a network; based on the predicted engagement level, the sensor data and the participant's fitness goal,
determining an exercise for the participant to perform during the conference call from a predefined lookup table of suggested exercises,
wherein the machine comprises a hardware processor coupled to a smartphone device, the smartphone device interfaced with a plurality of wearable devices worn by the participant, the plurality of wearable devices continuing to communicate real-time physiological sensor data to the smartphone device during the conference call,
wherein the hardware processor further monitors during the conference call, an audio sensor coupled to the smartphone device to determine current engagement level of the participant during the conference call,
wherein determining an exercise for the participant to perform during the conference call at least by:
automatically updating a decision determined based on the predicted engagement level that an exercise should not be recommended, to recommending the exercise based on the real-time physiological sensor data and the current engagement level of the participant during the conference call; and
transmitting the notification signal to the participant during the conference call.

8. The non-transitory computer readable storage medium of claim 7, wherein the data comprises a type of the conference meeting, a number of conference meetings being conducted at a time, agenda participation, context of the conference meeting, and a type of equipment used in the conference meeting.

9. The non-transitory computer readable storage medium of claim 7, wherein the labeled historical data comprise a type of a conference meeting, a number of conference meetings being conducted at a time, agenda participation, location, context of the conference meeting, and a type of equipment used in the conference meeting.

10. The non-transitory computer readable storage medium of claim 9, wherein the trained machine model is further trained based on sensor parameter data.

11. The non-transitory computer readable storage medium of claim 7, wherein the sensor data further comprises acceleration data from an acceleration sensor coupled to the smartphone device that measures acceleration.

12. The non-transitory computer readable storage medium of claim 7, wherein the trained machine model comprises a decision tree trained based on supervised machine learning algorithm.

13. A system of providing health activity for a participant in a conference call, comprising:
a predictive system executing on at least one hardware processor, the predictive system operable to train a machine model based on parameters labeled by analyzing historical pattern of engagement, the parameters comprising at least a type of a conference meeting, a number of conference meetings being conducted at a time, agenda participation, location, context of the conference meeting, and a type of equipment used in the conference meeting;
the predictive system receiving data associated with the conference call and location data specifying a location of the participant conducting the conference call, the predictive system predicting an engagement level of the participant that is to participate in the conference call based on the received data and the location data by executing the machine model with the received data and the location data as input to the machine model, the machine model trained to predict a level of engagement of the participant indicating how actively the participant participates in a meeting;
a reactive system executing on at least one hardware processor and coupled to at least one sensor device, the reactive system operable to detect sensor data comprising at least current physiological data associated with the participant via the at least one sensor device;
a decision making system executing on at least one hardware processor and operable to identify the participant's fitness goal stored in a network, and based on the predicted engagement level, the sensor data and the participant's fitness goal, determine an exercise for the participant to perform during the conference call from a predefined lookup table of suggested exercises,
the decision making system transmitting a notification signal to the participant to perform the exercise responsive to determining the exercise,
wherein the reactive system executes on a smartphone device, the smartphone device interfaced with a plurality of wearable devices worn by the participant, the plurality of wearable devices continuing to communicate real-time physiological sensor data to the smartphone device during the conference call,
wherein the reactive system further monitors during the conference call, an audio sensor coupled to the smartphone to determine current engagement level of the participant during the conference call,
wherein the reactive system automatically updates a decision determined based on the predicted engagement level that an exercise should not be recommended, to recommending the exercise based on the real-time physiological sensor data and the current engagement level of the participant during the conference call.

14. The system of claim 13, wherein the machine model comprises a decision tree trained based on supervised machine learning algorithm.

15. The system of claim 13, wherein the reactive system is further operable to detect acceleration data via an acceleration sensor device that measures acceleration.

* * * * *